US009149596B2

(12) United States Patent
Valcic et al.

(10) Patent No.: US 9,149,596 B2
(45) Date of Patent: Oct. 6, 2015

(54) RELEASE MECHANISM FOR PATIENT INTERFACE AND METHOD FOR RELEASING PATIENT INTERFACE

(75) Inventors: Zoran Valcic, Chatswood (AU); Bruce Richard Davies, Strathfield (AU); Huw Umberto Wallis, Gladesville (AU); Richard Sokolov, Earlwood (AU); Eric Siu, Strathfield (AU)

(73) Assignee: ResMed Limited, Bella Vista (AU)

( * ) Notice: Subject to any disclaimer, the term of this patent is extended or adjusted under 35 U.S.C. 154(b) by 1346 days.

(21) Appl. No.: 12/053,853

(22) Filed: Mar. 24, 2008

(65) Prior Publication Data

US 2008/0230069 A1 Sep. 25, 2008

Related U.S. Application Data

(60) Provisional application No. 60/969,723, filed on Sep. 4, 2007.

(30) Foreign Application Priority Data

Mar. 23, 2007 (AU) ................................ 2007901505

(51) Int. Cl.
*A62B 18/08* (2006.01)
*A61M 16/06* (2006.01)
(Continued)

(52) U.S. Cl.
CPC ............ *A61M 16/0683* (2013.01); *A44B 11/25* (2013.01); *A44B 11/2546* (2013.01); *A61M 16/0633* (2013.01); *A41D 2400/44* (2013.01)

(58) Field of Classification Search
CPC ............ A61M 16/06; A61M 16/0683; A61M 16/0694; A62B 9/04; A62B 18/02; A62B 18/025; A62B 18/06; A62B 18/084

USPC ............ 128/202.27, 207.11, 206.21; 24/170, 24/421, 573, 606, 579.09, 579.11, 573.11, 24/581.1, 614–616, 625; 49/301
See application file for complete search history.

(56) References Cited

U.S. PATENT DOCUMENTS 4,894,890 A * 1/1990 Kasai .......................... 24/579.09
4,945,614 A * 8/1990 Kasai .......................... 24/579.09
(Continued)

FOREIGN PATENT DOCUMENTS

WO WO 2004/030736 A1 4/2004

OTHER PUBLICATIONS

European Search Report and Opinion mailed Aug. 6, 2008 in European Appln. No. 08153251.7 (6 pages).
(Continued)

*Primary Examiner* — Valerie L Skorupa
(74) *Attorney, Agent, or Firm* — Nixon & Vanderhye P.C.

(57) ABSTRACT

A mechanism for releasing a mask from a patient's face includes a frame part including a male connection and a frame engagement portion for engaging a cooperating portion on a frame of the mask. A headgear part includes a female connection that is adapted to receive the male connection when the frame part is inserted into the headgear part, and a headgear engagement portion for engaging a cooperating portion on headgear of the mask. A cord has one end secured to the male connection, such that when the cord is pulled by the patient the male connection disengages from the female connection and consequently the frame part separates from the headgear part releasing the mask from the patient's face. A method of releasing a mask from a patient's face includes pulling a cord away from a frame of the mask to release a latch of the mask frame from a latch receiving portion of a headgear of the mask to release the latch from the latch receiving portion.

26 Claims, 11 Drawing Sheets

(51) Int. Cl.
  *A62B 18/02* (2006.01)
  *A44B 11/25* (2006.01)

(56) References Cited

U.S. PATENT DOCUMENTS

| | | | |
|---|---|---|---|
| 4,960,121 A * | 10/1990 | Nelson et al. | 128/206.24 |
| 5,259,093 A | 11/1993 | D'Annunzio | |
| 5,441,046 A | 8/1995 | Starr et al. | |
| 5,531,622 A | 7/1996 | Nealy | |
| 5,727,940 A * | 3/1998 | Wanzenbock | 433/5 |
| 6,374,826 B1 * | 4/2002 | Gunaratnam et al. | 128/206.27 |
| 6,422,238 B1 | 7/2002 | Lithgow | |
| 6,487,761 B2 * | 12/2002 | Van Tassel | 24/606 |
| 6,550,070 B2 * | 4/2003 | Wiegand | 2/421 |
| 6,615,834 B2 | 9/2003 | Gradon et al. | |
| 6,701,926 B2 | 3/2004 | Olsen et al. | |
| 6,789,541 B2 | 9/2004 | Olsen et al. | |
| 6,951,218 B2 | 10/2005 | Gradon et al. | |
| 7,900,630 B2 * | 3/2011 | Geiselhart et al. | 128/206.24 |
| 2002/0092140 A1 * | 7/2002 | Van Tassel | 24/614 |
| 2004/0112384 A1 | 6/2004 | Lithgow et al. | |
| 2006/0090760 A1 * | 5/2006 | Gradon et al. | 128/206.27 |
| 2008/0263836 A1 * | 10/2008 | Howell | 24/614 |

OTHER PUBLICATIONS

Communication dated Oct. 13, 2014 issued in European Application No. 08 153 251.7 (5 pages).

* cited by examiner

RELEASE MECHANISM FOR PATIENT INTERFACE AND METHOD FOR RELEASING PATIENT INTERFACE

CROSS REFERENCE TO RELATED APPLICATIONS

This application claims priority to Australian Provisional Application 2007901505, filed Mar. 23, 2007, and U.S. Provisional Application 60/969,723, filed Sep. 4, 2007, the entire contents of both applications being incorporated herein by reference.

FIELD OF THE INVENTION

The present invention relates to quick release mechanisms for allowing a patient interface, such as a Continuous Positive Airway Pressure (CPAP) mask, to be quickly and easily removed from a patient's face. More particularly, the invention relates to a clip for interconnection between a patient interface and headgear.

BACKGROUND OF THE INVENTION

CPAP masks are generally used for treating Obstructive Sleep Apnoea (OSA) and can take a number of different forms, such as a nasal, full-face or nasal prong type mask.

Various connection and release mechanisms or arrangements for masks are known. Examples of these include U.S. Pat. No. 6,422,238 (Lithgow), U.S. Pat. No. 5,441,046 (Starr et al.) and WO 2004/030736 (Gradon et al.).

SUMMARY OF THE INVENTION

Advantageously, a mask according to the invention can be removed from the patient's face quickly and easily in one continuous movement in the case of an emergency or discomfort (e.g. claustrophobia). To remove a mask from one's face, some other masks with quick release mechanisms require three movements (particularly when the patient is lying on their back), these being: (1) pulling the cord to undo/release the headgear, (2) gripping the mask, and (3) removing the mask from the face. Another advantage of the mask of the present invention is that it is removed by pulling the cord across one's face rather than outwardly. This is a natural, ergonomic hand/arm movement and so can be readily performed in an emergency. The mask also advantageously provides both a headgear clip and quick release clip in one clip. This allows the clip to be easily retrofitted to current mask products and may reduce the total number of parts required to achieve the same functionality. It should be appreciated that one or more of these advantages apply to the following aspects of the invention.

An aspect of the invention relates to a quick release mechanism for allowing a patient interface to be quickly and easily removed from the patient's face.

Another aspect of the invention relates to a clip for interconnection between a patient interface and headgear, the clip performing the function of both a headgear clip and a quick release clip. The patient interface can be quickly released and removed from a patient's face by simply pulling on a cord attached to the clip.

Yet another aspect of the invention relates to a pull cord for a patient mask which, when pulled by a patient, disengages one side of the headgear from the mask and pulls the mask off the patient's face.

According to a sample embodiment of the invention, a mechanism for releasing a mask from a patient's face comprises a frame part comprising a male connection and a frame engagement portion for engaging a cooperating portion on a frame of the mask; a headgear part comprising a female connection that is adapted to receive the male connection when the frame part is inserted into the headgear part, and a headgear engagement portion for engaging a cooperating portion on a headgear of the mask; and a cord having one end secured to the male connection, such that when the cord is pulled by the patient the male connection disengages from the female connection and consequently the frame part separates from the headgear part releasing the mask from the patient's face.

According to still another sample embodiment of the invention, a mechanism for releasing a mask from a patient's face comprises a first portion comprising a latch; a second portion comprising a latch receiving portion that is adapted to receive the latch when headgear of the mask is engaged with a frame of the mask; and a cord secured to the latch such that when the cord is pulled by the patient the latch disengages from the latch receiving portion and the mask is pulled off the patient's face.

According to a further sample embodiment of the invention, a mechanism for releasing a mask from a patient's face comprises a first portion comprising a latch; a second portion comprising a latch receiving portion that is adapted to receive the latch when a headgear of the mask is engaged with a frame of the mask; and a cord secured to the latch such that when the cord is pulled by the patient towards the frame, the latch disengages from the latch receiving portion and the first portion disengages from the second portion.

According to yet another sample embodiment of the invention, a mask comprises a mechanism as described above.

According to an even further sample embodiment of the invention, a clip assembly for releasing a mask from a patient's face comprises a first portion adapted for releasable attachment to a frame of the mask; and a second portion adapted for releasable attachment to headgear of the mask, the first and second portions together comprising a disconnection arrangement. The disconnection arrangement comprises a manual actuation member which when actuated by a patient causes the first portion to disconnect from the second portion and the mask to be pulled off the patient's face.

According to another sample embodiment of the invention, a clip assembly for releasing a mask from a patient's face comprises a first portion adapted for releasable attachment to a frame of the mask; and a second portion adapted for releasable attachment to headgear of the mask, the first and second portions together comprising a disconnection arrangement, wherein the disconnection arrangement comprises a pull cord. The mask can be pulled away from the patient's face by a single movement of pulling the pull cord.

According to a further sample embodiment of the invention, a mask comprises a frame having at least one male portion, the male portion comprising a latch; headgear having at least one female portion, the female portion comprising a latch receiving portion that is adapted to receive the latch when the male portion is inserted into the female portion; and a cord having one end secured to the latch, such that when the cord is pulled by the patient, the latch disengages from the latch receiving portion and the frame is pulled away from the patient's face.

According to yet another sample embodiment of the invention, a method of releasing a mask from a patient's face comprises pulling a cord toward a frame of the mask to release a latch of the mask frame from a latch receiving portion of a headgear of the mask to release the latch from the latch receiving portion.

These and other aspects will be described in or apparent from the following detailed description.

BRIEF DESCRIPTION OF THE DRAWINGS

The accompanying drawings facilitate an understanding of the various embodiments of the present invention. In such drawings:

FIGS. 31-34 show a sequence of side cross-sectional views that depict the releasing of the quick release mechanism of the headgear clip of FIG. 1, wherein FIG. 31 shows the clip in a connected state;

FIG. 32 shows a lip of the latching portion of the quick release mechanism being translated downwards;

FIG. 33 shows the lip disengaged from an aperture in the headgear part of the clip, and FIG. 34 shows the headgear part released from the frame part of the clip.

DETAILED DESCRIPTION OF ILLUSTRATED EMBODIMENTS

Figure 1:
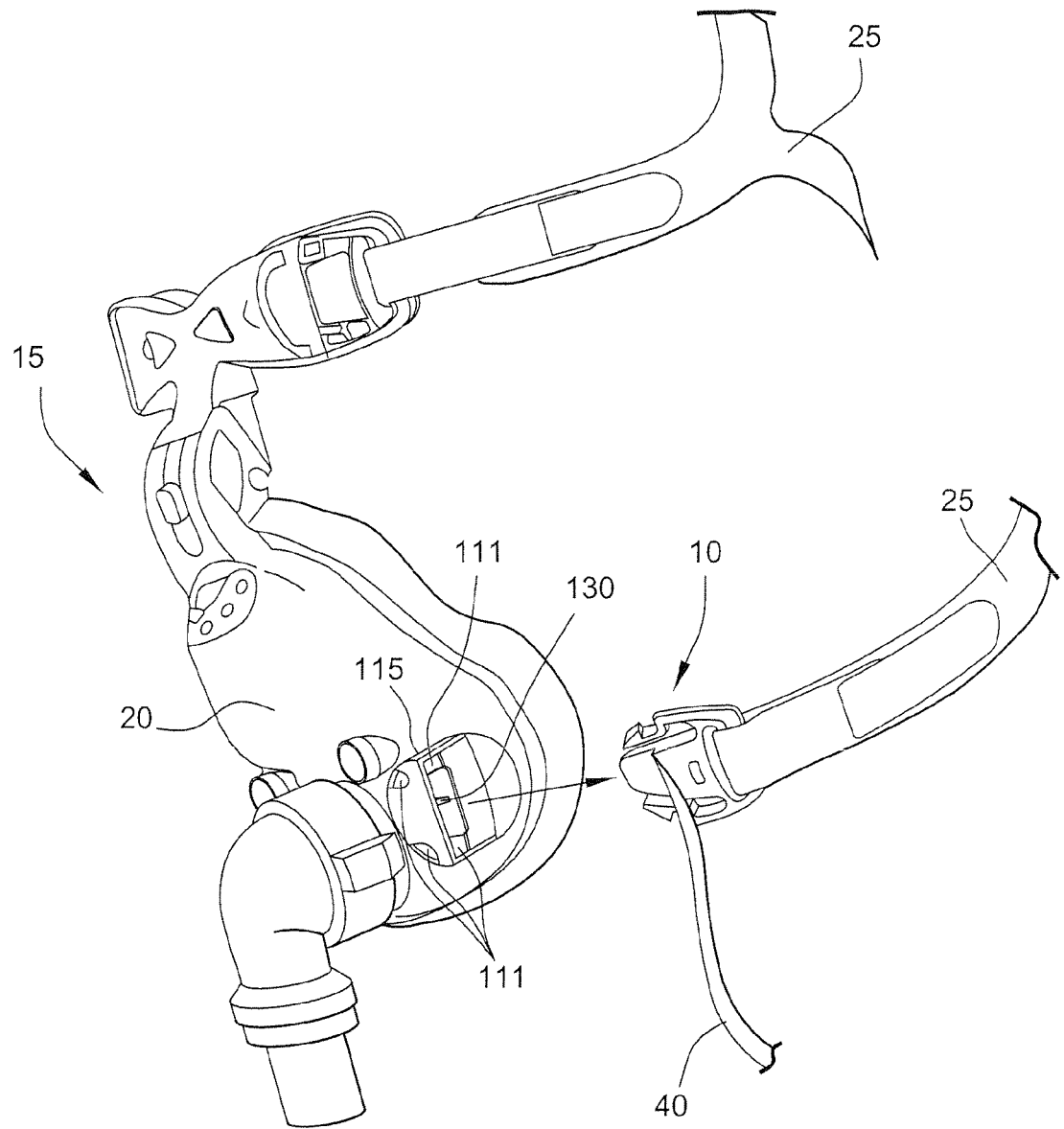
FIG. 1 shows a perspective view of a mask including a headgear clip having a pull-cord quick release mechanism in accordance with a first embodiment of the present invention.
Figure 2:
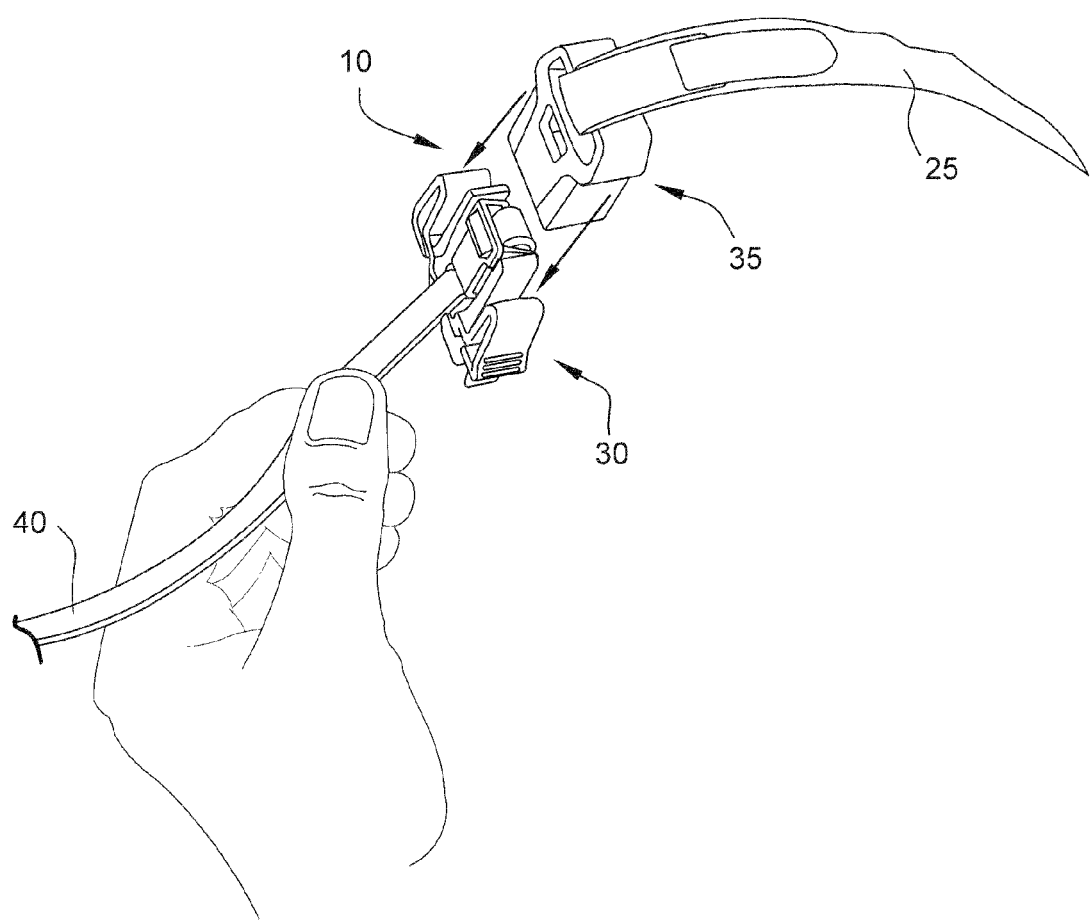
FIG. 2 shows a perspective view of the headgear clip of FIG. 1 where the quick release mechanism has been activated by a patient.
Figure 3:
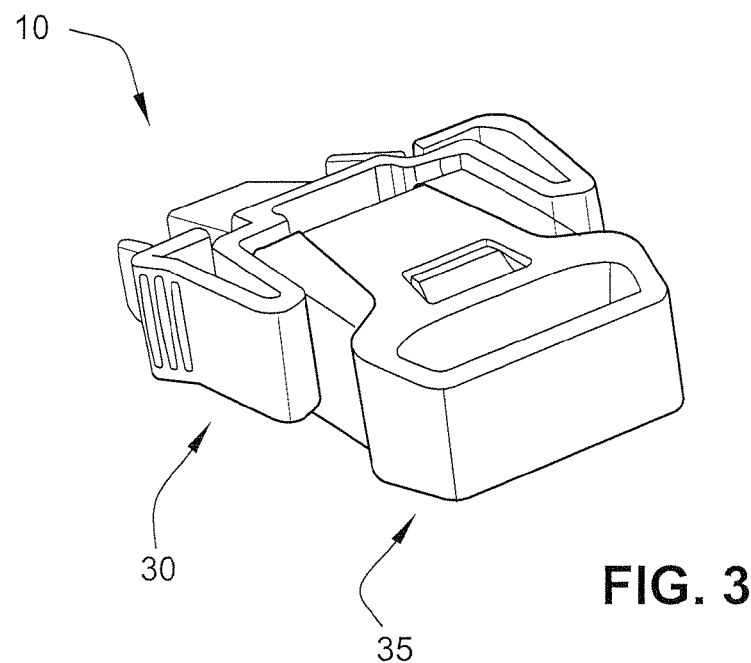
FIG. 3 shows a perspective view of the headgear clip of FIG. 1 where the quick release mechanism has not been activated.
Figure 4:
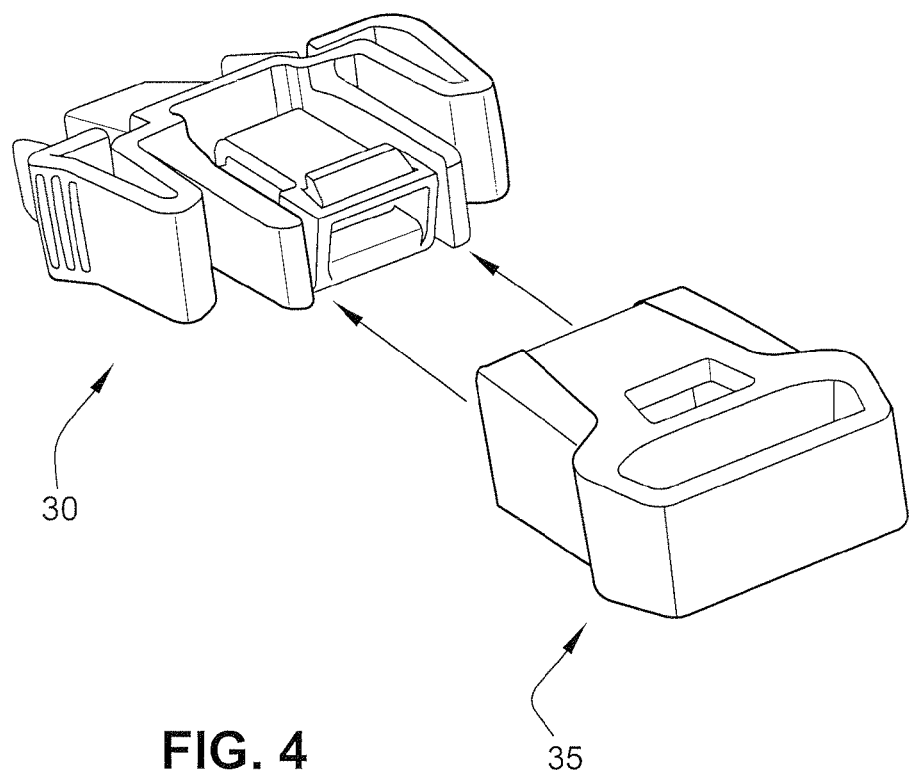
FIG. 4 shows a perspective view of the headgear clip of FIG. 1 where the quick release mechanism has been activated.
Figure 5:
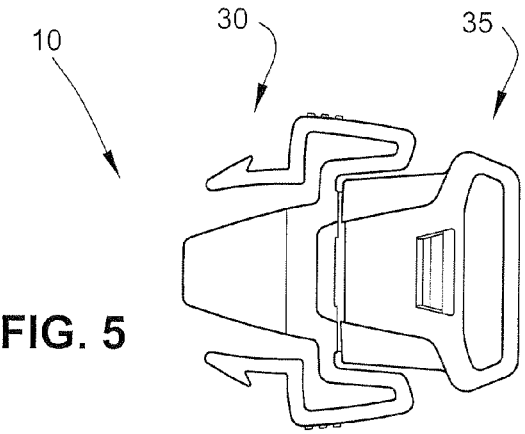
FIG. 5 shows a top view of the headgear clip of FIG. 1.
Figure 6:
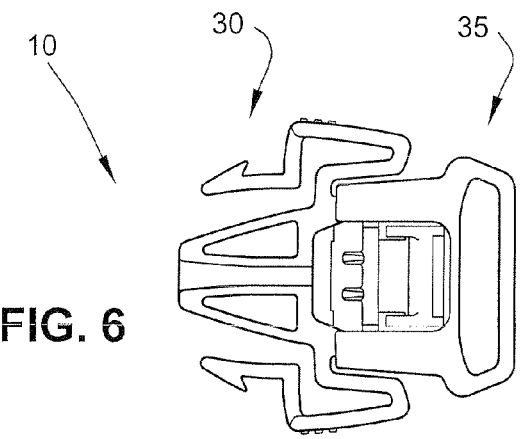
FIG. 6 shows a bottom view of the headgear clip of FIG. 1.
Figure 7:
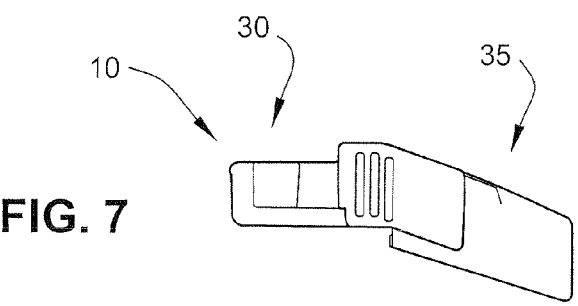
FIGS. 7 and 8 show left and right side views of the headgear clip of FIG. 1.
Figure 8:
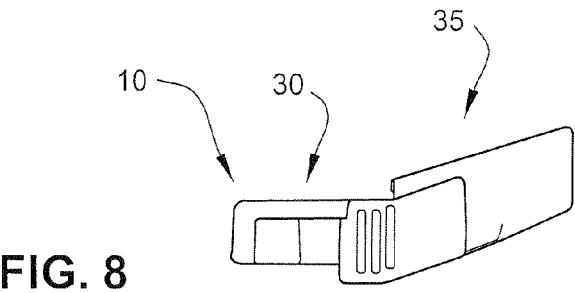
Figure 9:
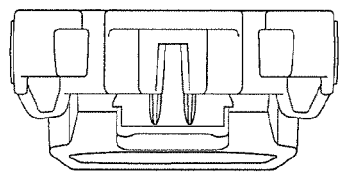
FIGS. 9 and 10 show front and rear end views of the headgear clip of FIG. 1.
Figure 10:
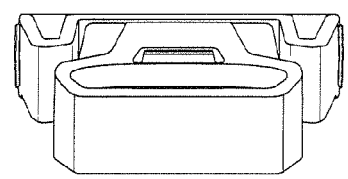
Figure 11:
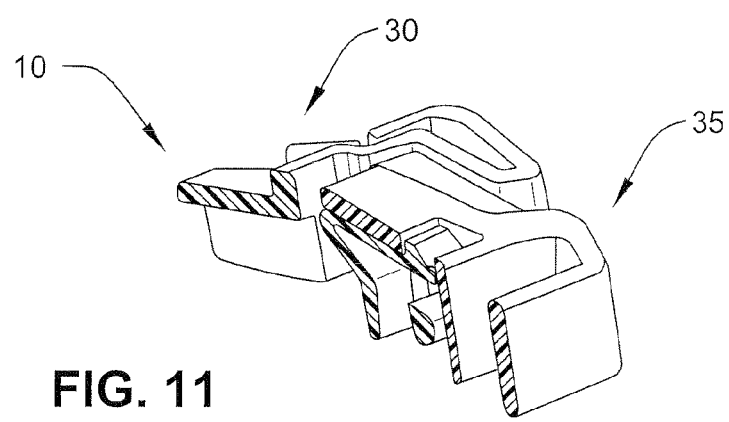
FIG. 11 shows a perspective cross-sectional view of the headgear clip of FIG. 1 where the quick release mechanism has not been activated.
Figure 12:
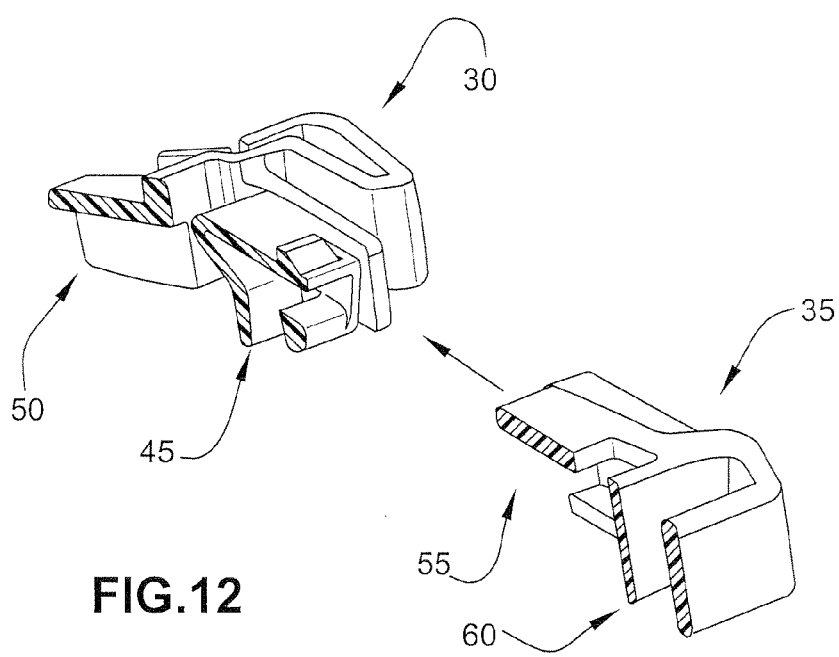
FIG. 12 shows a perspective cross-sectional view of the headgear clip of FIG. 1 where the quick release mechanism has been activated.
Figure 13:
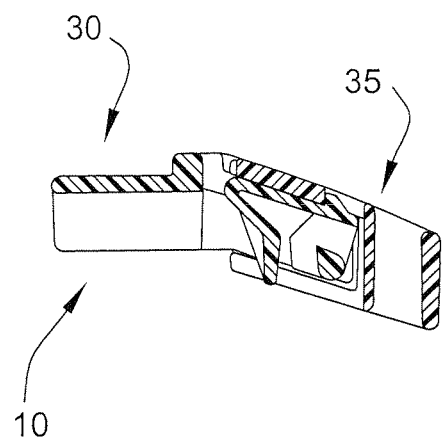
FIG. 13 shows a side cross-sectional view of the headgear clip of FIG. 1 where the quick release mechanism has not been activated.
Figure 14:
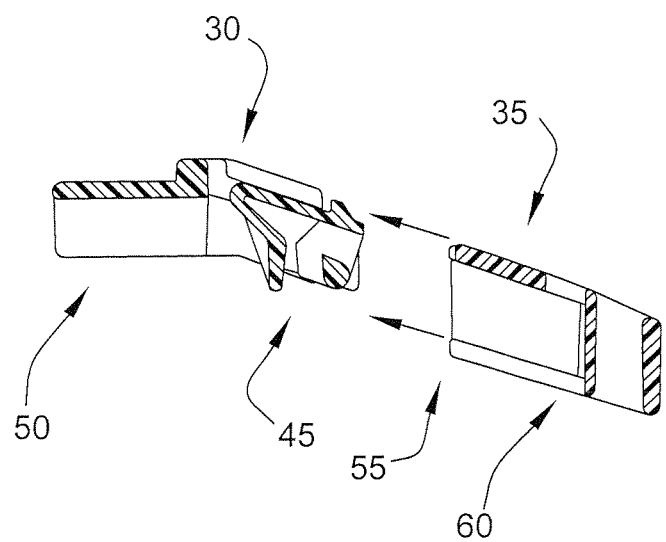
FIG. 14 shows a side cross-sectional view of the headgear clip of FIG. 1 where the quick release mechanism has been activated.
Figure 15:
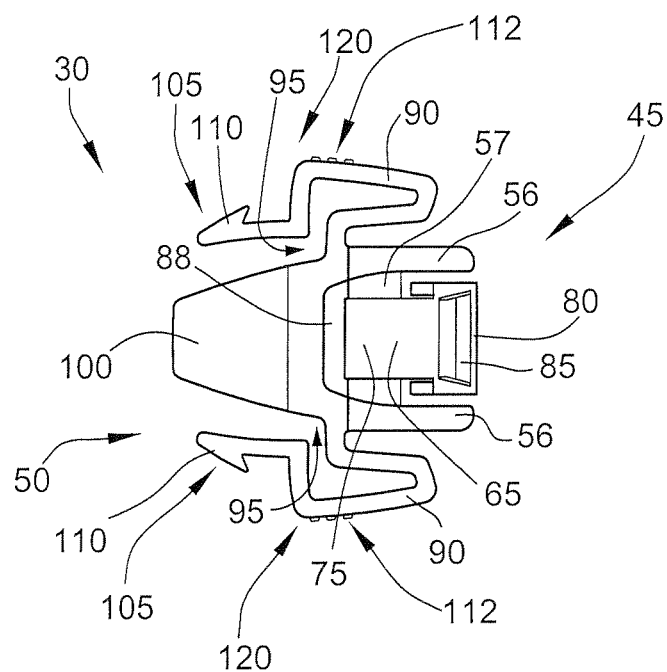
FIG. 15 shows a top view of a frame part of the headgear clip of FIG. 1.
Figure 16:
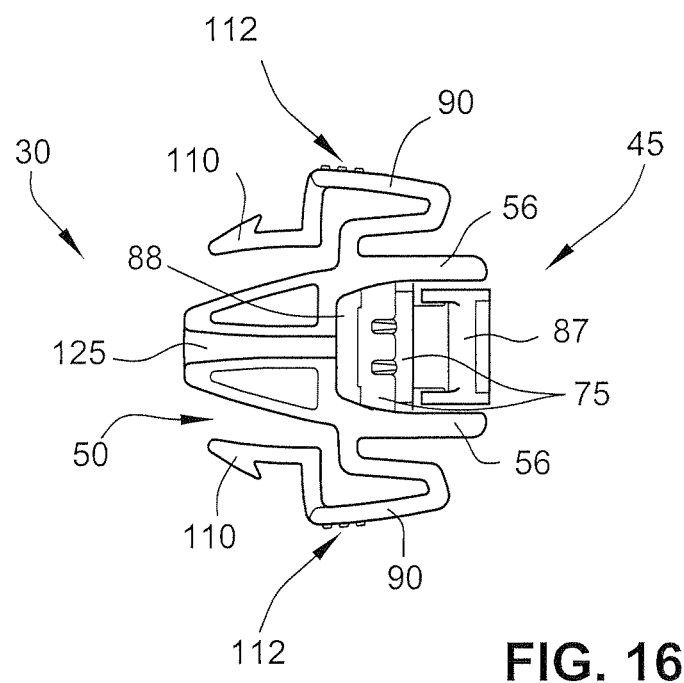
FIG. 16 shows a bottom view of the frame part of FIG. 15.
Figure 17:
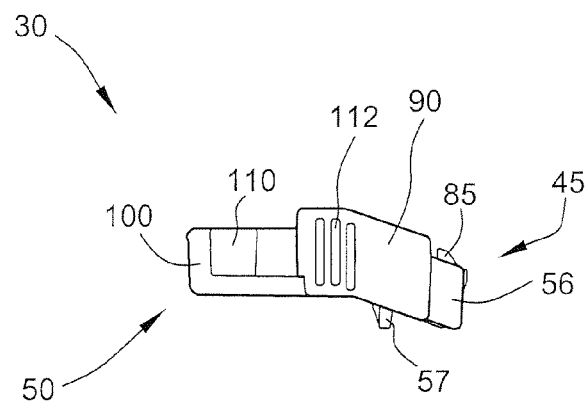
FIGS. 17 and 18 show left and right side views of the frame part of FIG. 15.
Figure 18:
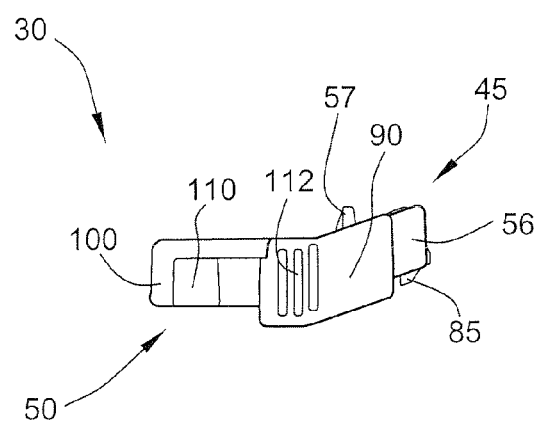
Figure 19:
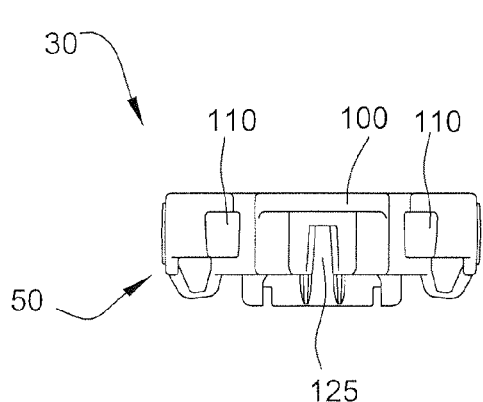
FIGS. 19 and 20 show front and rear end views of the frame part of FIG. 15.
Figure 20:
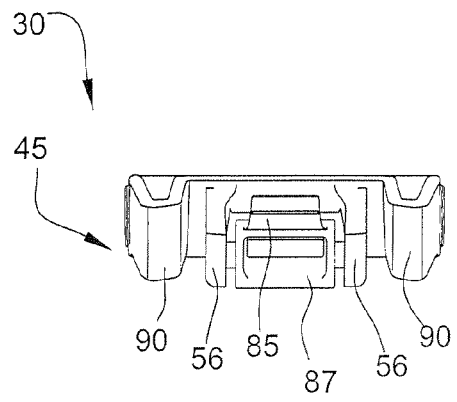
Figure 21:
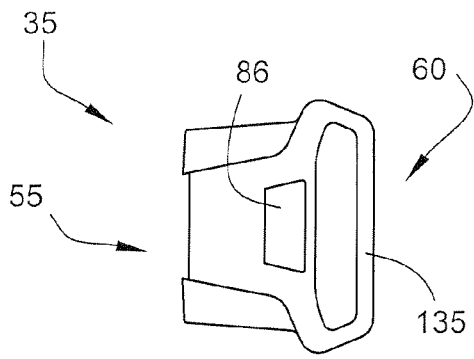
FIG. 21 shows a top view of a headgear part of the headgear clip of FIG. 1.
Figure 22:
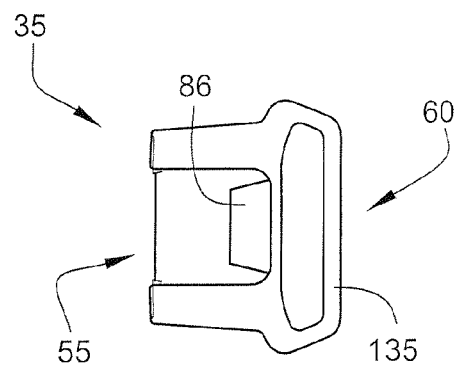
FIG. 22 shows a bottom view of the headgear part of FIG. 21.
Figure 23:
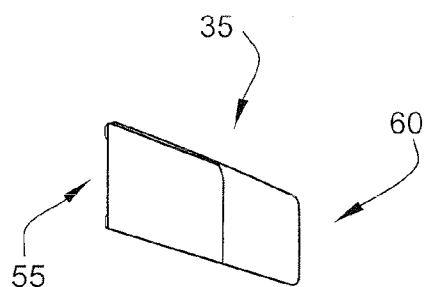
FIGS. 23 and 24 show left and right side views of the headgear part of FIG. 21.
Figure 24:
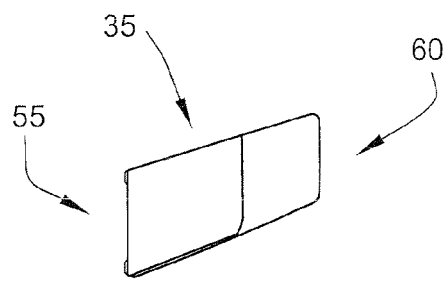
Figure 25:
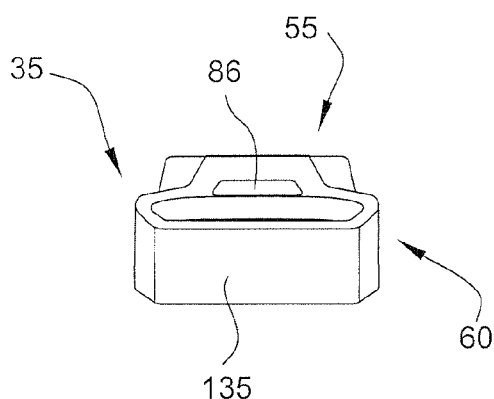
FIGS. 25 and 26 show front and rear end views of the headgear part of FIG. 21.
Figure 26:
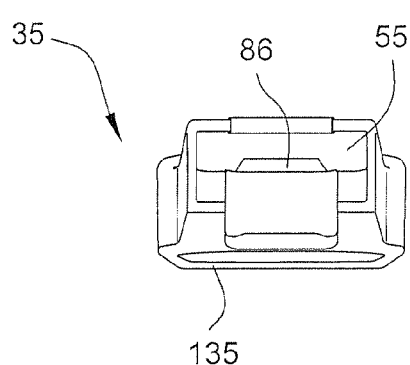
Figure 27:
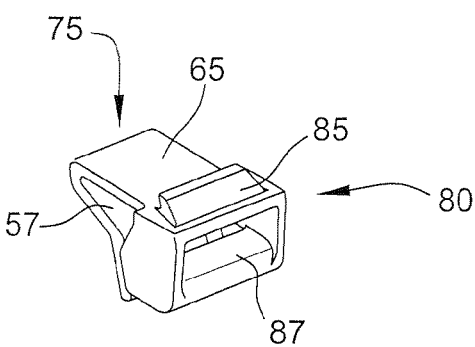
FIG. 27 shows a perspective view of a latching portion of the headgear clip of FIG. 1.
Figure 28:
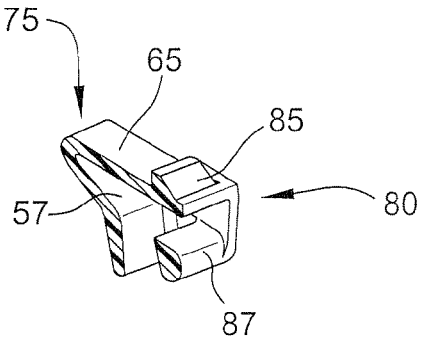
FIG. 28 shows a perspective cross-sectional view of the latching portion of FIG. 27.
Figure 29:
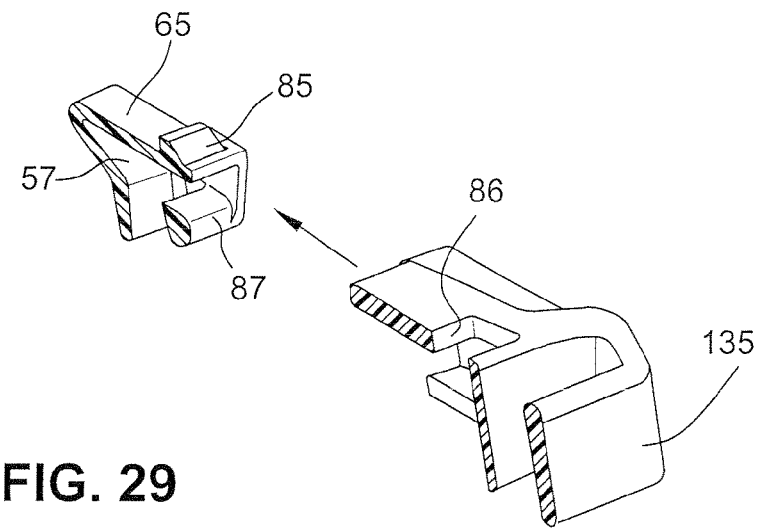
FIG. 29 shows a perspective cross-sectional view of the latching portion of FIG. 27 where the quick release mechanism has been activated.
Figure 30:
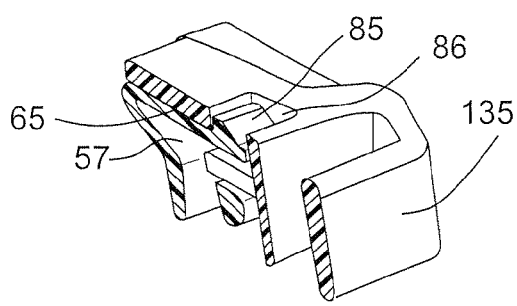
FIG. 30 shows a perspective cross-sectional view of the latching portion of FIG. 27 where the quick release mechanism has not been activated.

FIGS. 1-14 depict a quick release clip 10 for a patient interface or mask 15. The clip 10 is located between a frame 20 and headgear 25 of the mask 15 and allows a patient to disconnect the frame 20 from the headgear 25 and remove the frame 20 from their face. The clip 10 comprises a frame part 30, a headgear part 35 and a cord, wire, tape, or other flexible, elongate member, 40. The frame part 30 comprises a male connection 45, e.g. a latch, at one end and a frame engagement portion 50 at the other. The headgear part 35 comprises a female connection 55, e.g. a latch receiving portion, at one end and a headgear engagement portion 60 at the other.

Frame Part

The frame part 30 will now be described with reference to FIGS. 15-20 and 27-30. The male connection 45 is sized and adapted to be slidingly received within the female connection 55. The male connection 45 comprises two substantially parallel longitudinal side walls 56, a transverse wall 57 extending between and connecting the side walls 56 and an arm 65 extending longitudinally from the transverse wall 57. A proximal end 75 of the arm 65 is fixedly mounted to the transverse wall 57. A distal end 80 of the arm 65 can be resiliently displaced with respect to the proximal end 75. The distal end 80 includes an elongate lip 85 having a wedge-shaped cross-section that is configured to cooperate with an aperture 86 in the headgear part 35.

The overall length and width of the frame part 30 are approximately 20-35 mm, for example 28 mm, and 25-50 mm, for example 33 mm, respectively. The two substantially parallel side walls 56 are approximately 10-35 mm, for example 18 mm, apart. The arm 65 is approximately 10-20 mm, for example 13 mm, long and the elongate lip 85 is approximately 2-6 mm, for example 3.5 mm, wide and approximately 3-15 mm, for example 8 mm, long. The arm 65 is approximately 0.5-3 mm, for example 0.9 mm, thick and the lip 85 is approximately 0.7-3 mm, for example 1.2 mm, thick. The transverse wall 57 is approximately 5-16 mm, for example 11 mm, long.

Underneath the arm 65, substantially opposite the lip 85, a rectangular ring-like structure 87 is provided to which one end of the cord 40 is secured. The cord 40 then extends forwards (towards the frame engagement portion 50) underneath the arm 65, under the transverse wall 57 and up through an aperture 88 in the frame part 30. The aperture 88 is approximately 5-15 m, for example 10 mm, long and approximately 1-3 mm, for example 2 mm, wide.

The frame engagement portion 50 of the frame part 30 comprises two frog-like legs 90 that extend respectively from either side of a mid-section 95 of the frame part 30, and a central tongue 100. The legs 90 are shaped such that they initially extend rearwards in spaced relation to the male connection 45 then double back over themselves and extend approximately the length of the frame part 30 in spaced relation to the rearwardly extending portion of the legs 90 and then to the tongue 100.

Free ends 105 of the legs 90 include arrow-like portions 110 that are configured to engage apertures/recesses 111 provided by headgear clip receptacles 115 in the frame 20. The free ends 105 of the legs 90 are approximately 21 mm apart. Each leg 90 includes a gripping region 112 comprising a series of ribs adjacent the respective dog-leg portion 120. In use, the arrow-like portions 110 are resiliently displaced towards each other by manual clamping of the gripping regions 112 during insertion of the frame engagement portion 50 into the headgear clip receptacles 115. Once properly located, the legs can be released and the arrow-like portions locate in the apertures/recesses 111 to lock the frame engagement portion 50 to the frame 20. The free ends 105 of the legs 90 are approximately 3-8, for example 5 mm, wide and approximately 0.7-3 mm, for example 1.2 mm, thick.

The legs 90 also include dog-leg portions 120 that enable the legs 90 to run closer to the sides of the tongue 100. The dog-leg portions 120 are located approximately 5-16 mm, for example 11 mm, back from the front of the tongue 100.

The tongue 100 includes a convergent longitudinal recess 125 that is adapted to slidingly receive a wall portion 130 of the clip receptacles 115. Provision of the recess 125 and wall portion 130 aids location of the frame engagement portion 50 in the clip receptacles 115, which might otherwise be difficult for patient's who are not particularly dextrous. The tongue is approximately 4-11 mm, for example 7 mm, thick.

Headgear Part

The headgear part 35 will now be described with reference to FIGS. 21 to 26. The female connection 55 is configured to slidingly receive the male connection 45. Once properly located, the lip 85 of the arm 65 of the male connection 45 engages the aperture 86 and retains the male connection 45 substantially within the female connection 55. The headgear engagement portion 60 comprises a loop 135 having a width and height that are sufficient to allow it to slidingly receive a strap of the headgear 25.

The headgear part 35 is approximately 20-30 mm, for example 25 mm, wide at the headgear engagement portion 60 and approximately 10-30 mm, for example 19 mm, wide at the female connection 55. The headgear part 35 is approximately 15-40 mm, for example 23 mm, long and approximately 4-11 mm, for example 8 mm, thick. The general recess provided by the female connection 55 for receiving the male connection 45 is approximately 10-35 mm, for example 17 mm, wide and approximately 3-10 mm, for example 7 mm, high. The aperture 86 is approximately 2-6 mm, for example 3.6 mm, wide.

Functionality

Figure 31:
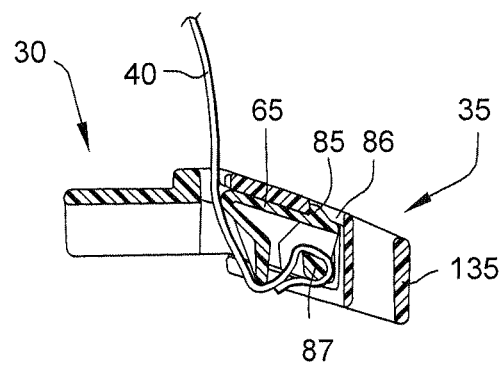

The functionality of the clip 10 will now be described with particular reference to FIGS. 31 to 34. FIG. 31 shows the clip 10 in normal use with the frame part 30 secured to the headgear part 35.

Figure 32:
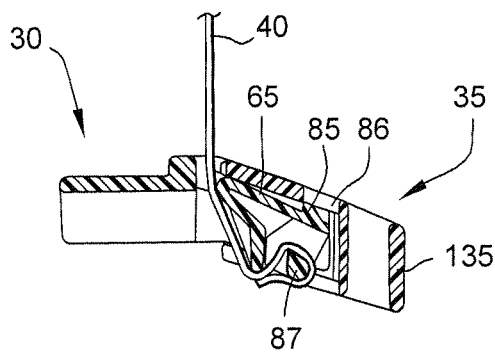

In FIG. 32, the patient or a clinician or other third party has decided to remove the mask 15 from the patient and so has pulled the cord 40. The cord 40 slides under the transverse wall 57 and pulls the arm 65 and lip 85 downwardly. This moves the lip 85 out of engagement with the aperture 86. Advantageously, the transverse wall 57 ensures that the force applied to the arm 65 by the cord 40 is in the correct direction (i.e. downwards) to bend the arm 65. Thus, the cord 40 can be pulled at a range of different angles including, from left-to-right (in use) an angular range of about 180 degrees and from up-to-down (in use) an angular range of about 120 degrees.

Figure 33:
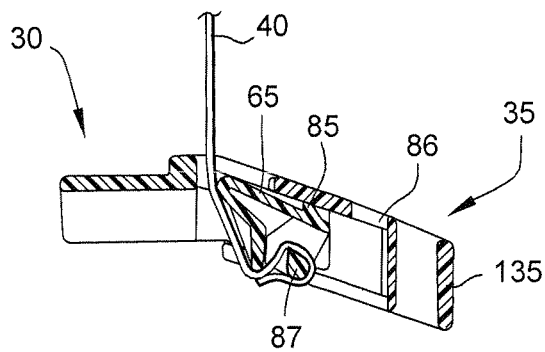
Figure 34:
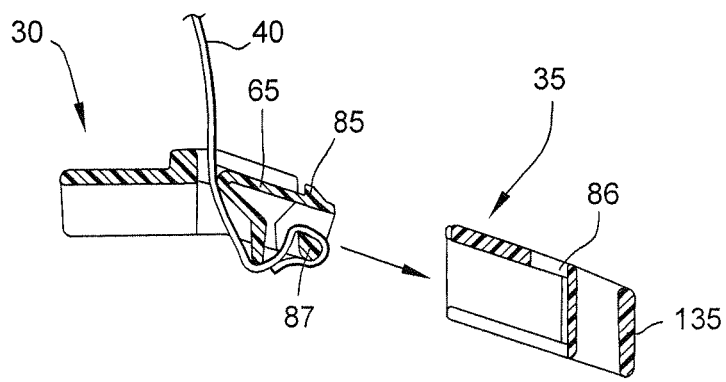

Referring to FIG. 33, by further pulling of the cord 40 the male connection 45 slides out of the female connection 55 until the frame part 30 is completely separated from the headgear part 35 as depicted in FIG. 34. By continuing the pulling action, the mask 15 can be pulled off the patient's face altogether.

It should be appreciated that the mask 15 can advantageously be released and removed from the patient's face by a single movement, that is, the pulling of the pull cord 40.

Advantageously, the mask 15 can be removed quickly and easily in the case of an emergency or even discomfort (e.g. claustrophobia). To remove the mask 15 from one's face, some other masks with quick release mechanisms require three movements (particularly when the patient is lying on their back), these being: (1) pulling the cord to undo/release the headgear, (2) gripping the mask, and (3) removing the mask from the face. Another advantage of the mask 15 is that it is removed by pulling the cord across one's face. This is a natural, ergonomic hand/arm movement and so can be readily performed in an emergency. Advantageously, the invention provides both a headgear clip and quick release clip in the one clip. This allows the clip to be easily retrofitted to current mask products and may reduce the total number of parts required to achieve the same functionality.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention.

For example, the cord 40 may include a loop along its length or at its free end to aid a patient in pulling it. In another embodiment, the cord 40 is replaced by a spring-loaded button or a lever. When the button is depressed or the lever is actuated the arm 65 is depressed and similar functionality is achieved to the cord 40. Preferably, the button faces away from the patient's face such that it can be easily accessed but cannot easily be accidentally depressed.

In yet another embodiment, the cord 40 may have a round cross-section to allow the cord to be pulled over a wider range of angles (left to right, up to down) and still allow the clip 10 to properly function. To better accommodate a round cord 40, the aperture 88 may take a convex conical form or a form that tapers from a smaller diameter to a larger diameter with large radius' around both edges.

In another variation, the lip 85 may have a different cross-section. Generally, the cross-section will enable better retainment of the headgear part 35 to the frame part 30 if the cross-section includes a retaining wall (i.e. a wall like the perpendicular wall provided by the wedge cross-section). Therefore, other suitable lip 85 cross-sections include a rectangular cross-section and a semi-bullet-shaped cross-section.

The dimensions provided in this specification could be altered by up to 20% or by up to 50% and a similar functionality still achieved.

Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A mechanism for releasing a mask from a patient's face, comprising:
a frame part comprising a male connection member and a frame engagement portion adapted to releasably engage a cooperating portion of the mask, a terminus of the frame engagement portion comprising an interface structure adapted to interlock with the cooperating portion of the mask, the interface structure comprising part of an arm and slot interlocking system;
a headgear part comprising a female connection member adapted to receive the male connection member when the frame part is inserted into the headgear part, and a headgear engagement portion adapted to engage a cooperating portion on a headgear of the mask, wherein the male connection member comprises a resilient arm having a lip and the female connection member comprises a slot that receives the arm and an aperture in the slot that receives the lip; and
a cord having one end secured to the male connection member, such that when the cord is pulled by the patient the male connection member disengages from the female connection member and consequently the frame part separates from the headgear part releasing the mask from the patient's face, wherein the cord is attached to the resilient arm whereby pulling on the cord disengages the lip of the resilient arm from the aperture of the slot to permit release of the mask from the patient's face and the frame part includes a transverse wall adapted to direct a tension force on the cord to disengage the lip from the aperture when the cord is pulled in a range of about 180 degrees extending from left to right and in a range of about 120 degrees extending up-to-down,
wherein the interface structure of the frame part comprises a tongue and resilient legs on opposite sides of the tongue, the cooperating portion of the mask comprises a receptacle integral with a frame of the mask, and the tongue and the resilient legs are insertable into the receptacle.

2. A mechanism according to claim 1, wherein ends of the resilient legs are received in apertures in the receptacle.

3. A mechanism according to claim 1, wherein the tongue includes a groove that receives a wall portion of the receptacle so that the frame part is insertable in the receptacle in only one configuration.

4. A mechanism according to claim 1, wherein the cord has a round cross section.

5. A mechanism according to claim 1, wherein a free end of the cord is unattached.

6. A mechanism according to claim 5, wherein the free end of the cord includes a loop.

7. A mechanism according to claim 1, wherein the arm of the male connection member is connected to the frame part in a cantilevered fashion and wherein the one end of the cord is connected to the free end of the arm.

8. A mechanism as defined in claim 1, wherein the frame engagement portion is a clip and the cooperating portion on the frame is a clip receptacle that is adapted to releasably lock to the clip.

9. A mechanism according to claim 1, wherein the frame part is configured to disconnect from the headgear part without separating from the cooperating portion.

10. A mechanism according to claim 1, wherein an engagement between the frame part and the cooperating portion is configured to remain unchanged when the frame part and the headgear part are separated.

11. A mechanism according to claim 1, wherein, the frame engagement portion is adapted to be fixed against movement relative to a frame of the mask when the frame engagement portion is engaged with the cooperating portion which is configured to be fixed against movement relative to a frame of the mask.

12. A mechanism according to claim 1, wherein the frame engagement portion and the male connection member of the frame part are positioned on opposite sides of the frame part.

13. A mask comprising:
a mechanism for releasing the mask from a patient's face, the mechanism comprising:
a frame part comprising a male connection member and a frame engagement portion adapted to releasably engage a cooperating portion of the mask, a terminus of the frame engagement portion comprising an interface structure adapted to interlock with the cooperating portion of the mask, the interface structure comprising part of an arm and slot interlocking system;
a headgear part comprising a female connection member adapted to receive the male connection member when the frame part is inserted into the headgear part, and a headgear engagement portion adapted to engage a cooperating portion on a headgear of the mask, wherein the male connection member comprises a resilient arm having a lip and the female connection member comprises a slot that receives the arm and an aperture in the slot that receives the lip; and
a cord having one end secured to the male connection member, such that when the cord is pulled by the patient the male connection member disengages from the female connection member and consequently the frame part separates from the headgear part releasing the mask from the patient's face, wherein the cord is attached to the resilient arm whereby pulling on the cord disengages the lip of the resilient arm from the aperture of the slot to permit release of the mask from the patient's face and the frame part includes a transverse wall adapted to direct a tension force on the cord to disengage the lip from the aperture when the cord is pulled in a range of about 180 degrees extending from left to right and in a range of about 120 degrees extending up-to-down.

14. A mask comprising:
a mechanism for releasing the mask from a patient's face, the mechanism comprising:
a first portion comprising a latch, the first portion having a continuous structure with a terminus configured to directly engage and releasably attach to a frame of the mask;
a second portion comprising a latch receiving portion that is adapted to receive the latch when headgear of the mask is engaged with the frame of the mask; and
a cord secured to the latch such that when the cord is pulled by the patient the latch disengages from the latch receiving portion and the mask is pulled off the patient's face, wherein the latch comprises an arm that is connected to the first portion in a cantilevered fashion and wherein one end of the cord is connected to a free end of the arm and the latch comprises a wall configured to direct a tension force on the cord to disengage the latch from the latch receiving portion when the cord is pulled in a range of about 180 degrees extending from left to right and in a range from about 120 degrees extending up-to-down.

15. A mask assembly comprising:
a cushion configured to form a seal with a face of a patient;
a frame to support the cushion;
headgear for mounting the mask assembly on the patient's head; and
a clip assembly releasably connecting the headgear to the frame, the clip assembly comprising:
 a first portion adapted for releasable attachment to a frame of the mask; and
 a second portion adapted for releasable attachment to headgear of the mask, the first and second portions together comprising a disconnection arrangement, wherein the disconnection arrangement comprises a manual actuation member which when actuated by a patient causes the first portion to disconnect from the second portion and the mask to be pulled off the patient's face, wherein the actuation member comprises a pull cord, one end of the pull cord being secured to the first portion, the arrangement being such that when the pull cord is pulled while the first portion is fixed against movement relative to the frame in a range of about 180 degrees extending left to right and in a range of about 120 degrees extending up-to-down, the first portion is disconnected from the second portion and the mask is pulled off the patient's face,
wherein the first portion is adapted to connect to the frame of the mask and disconnect from the second portion in the same direction relative to the second portion.

16. A mask assembly according to claim 15, wherein a second end of the pull cord is unattached.

17. A mask assembly according to claim 15, wherein the first portion of the clip assembly comprises a component engaging member located at a terminus of the first portion, the component engaging member being adapted to engage a component of the mask when the first portion is attached to the frame, such that when the first portion is attached to the frame, the first portion terminates at a point of engagement between the component engaging member and the component of the mask.

18. A mask assembly according to claim 17, wherein the first portion of the clip assembly is configured to cooperate with the component of the mask to prevent movement of the first portion relative to the frame when the first portion is attached to the frame.

19. A mask assembly according to claim 18, wherein the first portion of the clip assembly further comprises a male connector and the second portion comprises a female connector configured to receive the male connector.

20. A mask assembly according to claim 19, wherein the mask engaging portion of the clip assembly is configured to releasably engage the mask.

21. A mask assembly according to claim 15, wherein the frame comprises a cooperating member configured to receive the first portion of the clip assembly.

22. A mask assembly according to claim 15, wherein a terminus of the first portion of the clip assembly comprises a latch portion of an interlocking latch arrangement adapted for releasable attachment to the frame of the mask.

23. A mask assembly according to claim 22, wherein the first portion of the clip assembly is continuous and is adapted to engage the second portion at an end opposite the terminus.

24. A mask assembly comprising:
a cushion configured to form a seal with a face of a patient;
a frame to support the cushion;
headgear for mounting the mask assembly on the patient's head; and
a clip assembly releasably connecting the headgear to the frame and comprising:
 a first portion releasably attached to the frame such that when attached to the frame, the first portion cooperates with the frame to prevent all movement of the first portion relative to the frame; and
 a second portion releasably attached to the headgear, the first and second portions together comprising a disconnection arrangement, wherein the disconnection arrangement comprises a pull cord, wherein the mask can be pulled away from the patient's face by a single movement of pulling the pull cord in a range of about 180 degrees extending left to right and in a range of about 120 degrees extending up-to-down,
wherein the clip assembly releasably attaches to the frame at a first location and gas is supplied to the frame at a second location separate from the first location.

25. A mask assembly according to claim 24, wherein the frame comprises a cooperating member configured to receive the first portion of the clip assembly.

26. A mask assembly according to claim 25, wherein the first portion of the clip assembly releasably attaches to the frame at a terminus of the first portion.

* * * * *